United States Patent [19]
Konishi et al.

[11] Patent Number: 4,564,386
[45] Date of Patent: Jan. 14, 1986

[54] TRIFLUOROMETHANESULFONANILIDES, AND THEIR PRODUCTION AND USE

[75] Inventors: Hiroyuki Konishi; Shunichi Hashimoto; Hiromichi Oshio, all of Osaka, Japan

[73] Assignee: Sumitomo Chemical Company, Limited, Osaka, Japan

[21] Appl. No.: 520,211

[22] Filed: Aug. 4, 1983

Related U.S. Application Data

[63] Continuation-in-part of Ser. No. 404,705, Aug. 3, 1982.

[51] Int. Cl.⁴ .................. A01N 41/00; C07C 143/72
[52] U.S. Cl. ........................ 71/103; 564/82; 71/88; 544/159; 260/543 R
[58] Field of Search .............. 564/82; 71/103

[56] References Cited

U.S. PATENT DOCUMENTS

| | | | |
|---|---|---|---|
| 2,885,435 | 5/1959 | Pursglove | 71/103 |
| 3,234,255 | 2/1966 | Hackman et al. | 71/103 |
| 3,439,018 | 4/1969 | Brookes et al. | 71/103 |
| 3,518,076 | 6/1970 | Wright | 71/103 |
| 3,576,872 | 4/1971 | Singhal | 71/103 |
| 3,672,864 | 6/1972 | Maravetz | 71/103 |
| 3,734,710 | 5/1973 | Lukaszczyk et al. | 71/103 |
| 3,920,444 | 11/1975 | Harrington et al. | 71/103 |
| 3,977,861 | 8/1976 | Kawamura et al. | 71/103 |
| 4,005,141 | 1/1977 | Moore et al. | 564/82 |
| 4,070,176 | 1/1978 | Oshio et al. | 71/103 |

Primary Examiner—Glennon H. Hollrah
Assistant Examiner—Andrew Duff Meikle
Attorney, Agent, or Firm—Birch, Stewart, Kolasch & Birch

[57] ABSTRACT

A herbicidal composition which comprises as an active ingredient a trifluoromethanesulfonanilide of the formula:

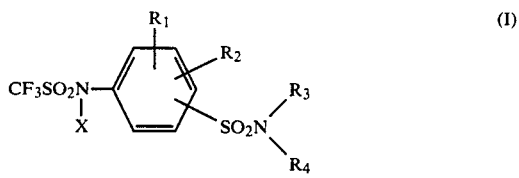

wherein $R_1$ and $R_2$ are, the same or different, each a hydrogen atom, a halogen atom or a $C_1$–$C_4$ alkyl group, $R_3$ and $R_4$ are, the same or different, each a hydrogen atom, a $C_1$–$C_4$ alkyl group, a $C_3$–$C_6$ cycloalkyl group, a $C_3$–$C_4$ alkenyl group, a $C_3$–$C_5$ alkynyl group, a $C_1$–$C_4$ alkoxy group, a $C_6$–$C_7$ aralkyl group, a $C_1$–$C_4$ alkoxy($C_1$–$C_4$)alkyl group or a $C_2$–$C_5$ acyl group or they may be combined together with the nitrogen atom to form a morpholino group and X is a $C_2$–$C_5$ acyl group, provided that $R_3$ and $R_4$ are not simultaneously a hydrogen atom or a $C_2$–$C_5$ acyl group.

9 Claims, No Drawings

TRIFLUOROMETHANESULFONANILIDES, AND THEIR PRODUCTION AND USE

This is a continuation-in-part application of our co-pending application Ser. No. 404,705 filed on Aug. 3, 1982.

The present invention relates to trifluoromethanesulfonanilides, and their production and use.

The said trifluoromethanesulfonanilides are representable by the formula:

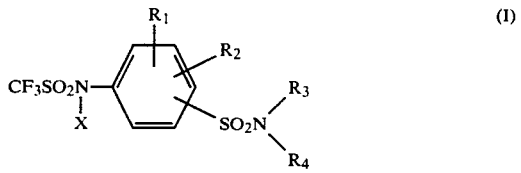

wherein $R_1$ and $R_2$ are, the same or different, each a hydrogen atom, a halogen atom (e.g. chlorine, bromine, iodine, fluorine) or a $C_1$-$C_4$ alkyl group and $R_3$ and $R_4$ are, the same or different, each a hydrogen atom, a $C_1$-$C_4$ alkyl group, a $C_3$-$C_6$ cycloalkyl group, a $C_3$-$C_4$ alkenyl group, a $C_3$-$C_5$ alkynyl group, a $C_1$-$C_4$ alkoxy group, a $C_7$-$C_8$ aralkyl group (e.g. benzyl, phenethyl), a $C_1$-$C_4$ alkoxy($C_1$-$C_4$)alkyl group or a $C_2$-$C_5$ acyl group such as $C_2$-$C_5$ alkanoyl or they may be combined together with the nitrogen atom to form a morpholino group, and X is a $C_2$-$C_5$ acyl group such as $C_2$-$C_5$ alkanoyl, provided that $R_3$ and $R_4$ are not simultaneously a hydrogen atom or a $C_2$-$C_5$ acyl group.

Particularly preferred are those of the formula (I) wherein $R_1$, $R_2$, $R_3$ and $R_4$ are each a hydrogen atom, a methyl group, an ethyl group or a t-butyl group and X is a $C_2$-$C_4$ alkanoyl group.

It is known that certain kinds of trifluoromethanesulfonanilides are effective as herbicides. For instance, the herbicidal use of 2-methyl-4-phenylsulfonyltrifluoromethanesulfonanilide (British Pat. No. 1,306,564) and 4-sulfamoyl-trifluoromethanesulfonanilide (U.S. Pat. No. 3,639,474), etc. are known. However, their herbicidal effect is still not always satisfactory.

It has now been found that the trifluoromethanesulfonanilides (I) of the invention show a strong herbicidal activity against a wide variety of weeds including Graminaceous weeds, broad-leaved weeds and Cyperaceae weeds at small doses and do not produce any material phytotoxicity on various agricultural crops such as soybeans, cotton and sugarbeet by pre-emergence soil treatment prior to emergence of weeds as well as post-emergence foliar treatment after emergence. Examples of Graminaceous weeds against which the sulfonanilide derivatives (I) show a herbicidal activity are barnyardgrass (*Echinochloa crus-galli*), green foxtail (*Setaria viridis*), annual bluegrass (*Poa annua*), wild oat (*Avena fatua*), Johnsongrass (*Sorghum halepense*), Johnsongrass rhizome (*Sorghum halepense*), etc. Examples of broad-leaved weeds are tall morningglory (*Ipomoea purpurea*), velvetleaf (*Abutilon theophrasti*), common chickweed (*Stellaria media*), pineappleweed (*Matricaria spp.*), wild mustard (*Brassica kaber*), etc. Examples of Cyperaceae weeds are purple nutsedge (*Cyperus rotundus*), yellow nutsedge (*Cyperus esculentus*), etc.

Accordingly, the trifluoromethanesulfonanilides (I) can be used as herbicides applicable for the fields of crops and vegetables, or an orchard, lawn, pasture, tea garden, mulberry field, rubber plantation, forest, non-agricultural field, etc.

A typical procedure for preparation of the trifluoromethanesulfonanilides (I) is shown below.

A trifluoromethanesulfonanilide of the formula:

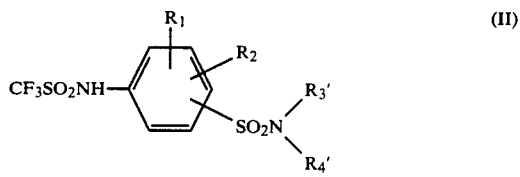

wherein $R_1$ and $R_2$ are each as defined above and $R_3'$ and $R_4'$ are, the same or different, each a hydrogen atom, a $C_1$-$C_4$ alkyl group, a $C_3$-$C_6$ cycloalkyl group, a $C_3$-$C_4$ alkenyl group, a $C_3$-$C_5$ alkynyl group, a $C_1$-$C_4$ alkoxy group, a $C_6$-$C_7$ aralkyl group or a $C_1$-$C_4$ alkoxy($C_1$-$C_4$)alkyl group or they may be combined together with the nitrogen atom to form a morpholino group, $R_3'$ and $R_4'$ being not simultaneously hydrogen, is reacted with an acyl halide (e.g. chloride, bromide) of the formula:

$$X-Z \qquad (III)$$

wherein X is as defined above and Z is a halogen atom (e.g. chlorine, bromine) to give the trifluoromethanesulfonanilide (I).

In the above reaction, the acyl halide (III) may be employed in an amount of one to two equivalents with respect to the trifluoromethanesulfonanilide (II). Usually, the reaction is carried out in an inert solvent such as a hydrocarbon (e.g. benzene, toluene, xylene), an ether (e.g. tetrahydrofuran, dimethoxyethane), a halogenated hydrocarbon (e.g. chlorobenzene, dichlorobenzene, methylene chloride, ethylene dichloride, chloroform, carbon tetrachloride), N,N-dimethylacetamide, dimethylformamide or dimethyl sulfoxide, preferably in the presence of a base such as an organic base (e.g. triethylamine, tributylamine, pyridine, N-methylmorpholine, N,N-dimethylaniline, N,N-diethylaniline) or an inorganic base (e.g. potassium carbonate, sodium carbonate, potassium hydroxide, sodium hydroxide). The reaction proceeds ordinarily at a temperature of from the freezing point of the solvent to the boiling point of the solvent, preferably of 0° to 80° C., and can be accomplished within a period of 30 minutes to 10 hours.

The starting trifluoromethanesulfonanilide (II) is obtainable by the following procedure.

A sulfonanilide of the formula:

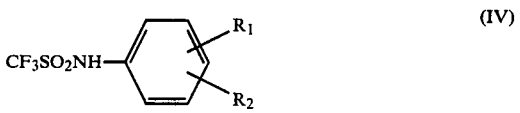

wherein $R_1$ and $R_2$ are each as defined above is reacted with chlorosulfonic acid to give a benzenesulfonyl chloride of the formula:

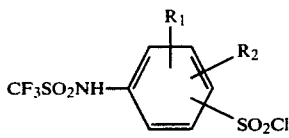

wherein $R_1$ and $R_2$ are each as defined above.

In the above reaction, the chlorosulfonic acid may be used in an amount of two equivalents or more with respect to the sulfonanilide (IV). The reaction is usually carried out in an inert solvent such as a halogenated hydrocarbon (e.g. methylene chloride, ethylene dichloride, chloroform, carbon tetrachloride) at a temperature of 0° to 100° C.

Then, the benzenesulfonyl chloride (V) is reacted with an amine of the formula:

wherein $R_3'$ and $R_4'$ are each as defined above to give the trifluoromethanesulfonanilide (II).

In the above reaction, the amine (VI) may be used in an amount of one to two equivalents with respect to the benzenesulfonyl chloride (V). The reaction is usually effected in an inert solvent such as a hydrocarbon (e.g. benzene, toluene, xylene), an ether (e.g. tetrahydrofuran, dimethoxyethane), a halogenated hydrocarbon (e.g. chlorobenzene, dichlorobenzene, methylene chloride, ethylene dichloride, chloroform, carbon tetrachloride), N,N-dimethylacetamide, dimethylformamide, dimethyl sulfoxide or water, if necessary, in the presence of a base such as an organic base (e.g. triethylamine, tributylamine, pyridine, N-methylmorpholine, N,N-diethylaniline, N,N-dimethylaniline) or an inorganic base (e.g. potassium carbonate, sodium carbonate, potassium hydroxide, sodium hydroxide) at a temperature of from the freezing point of the solvent to the boiling point of the solvent, preferably of 0° to 70° C. Normally, the reaction is accomplished within a period of 30 minutes to 10 hours.

Alternatively, the trifluoromethanesulfonanilide (II) is prepared by reacting an aminobenzenesulfonamide of the formula:

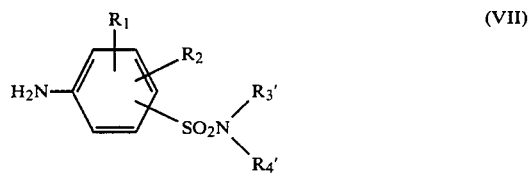

wherein $R_1$, $R_2$, $R_3'$ and $R_4'$ are each as defined above with trifluoromethanesulfonic anhydride or trifluoromethanesulfonyl halide (e.g. chloride).

In the reaction, the trifluoromethanesulfonic anhydride or trifluoromethanesulfonyl halide (e.g. chloride) may be employed in an equivalent or more amount with respect to the aminobenzenesulfonamide (VII). The reaction is usually effected in the presence or absence of any inert solvent such as a halogenated hydrocarbon (e.g. methylene chloride, ethylene dichloride, chloroform), an ether (e.g. tetrahydrofuran, dimethoxyethane), N,N-dimethylacetamide, dimethylformamide or dimethyl sulfoxide, preferably in the presence of a base such as an organic base (e.g. triethylamine, tributylamine, pyridine, N-methylmorpholine, N,N-dimethylaniline, N,N-diethylaniline) or an inorganic base (e.g. potassium carbonate, sodium carbonate, sodium hydroxide, potassium hydroxide). The reaction normally proceeds at a temperature of the freezing point of the solvent to the boiling point of the solvent, preferably of 0° to 80° C., and can be accomplished within a period of 30 minutes to 10 hours.

Practical and presently preferred embodiments of the production of the objective trifluoromethanesulfonanilides (I) are illustratively shown below.

EXAMPLE 1

To a solution of N,N-dimethyl-3-methyl-4-(trifluoromethanesulfonamido)benzenesulfonamide (1.5 g) and triethylamine (0.65 g) in tetrahydrofuran (40 ml), acetyl chloride (0.51 g) was added, and the resultant mixture was stirred at room temperature for 3 hours. The reaction mixture was concentrated and solidified with water. The solidified product was recrystallized from a mixture of ethanol and toluene to give 1.29 g of N,N-dimethyl-3-methyl-4-(N-acetyl-N-trifluoromethanesulfonylamino)benzenesulfonamide (Compound No. 21). M.P., 148°–148.5° C.

EXAMPLE 2

To a solution of N-propargyl-2,4-dimethyl-5-(trifluoromethanesulfonamido)benzenesulfonamide (1.5 g) and triethylamine (1.2 g) in tetrahydrofuran (20 ml), acetyl chloride (1.0 g) was added, and the resultant mixture was allowed to stand at room temperature overnight. The reaction mixture was concentrated, admixed with 5% hydrochloric acid and extracted with chloroform. The extract was concentrated to give an oily substance, which was purified by silica gel chromatography to give 1.4 g of N-acetyl-N-propargyl-2,4-dimethyl-5-(N-acetyl-N-trifluoromethanesulfonylamino)benzenesulfonamide (Compound No. 10). $n_D^{20}$ 1.5209.

EXAMPLE 3

To a solution of N-methyl-2,4-dimethyl-5-(trifluoromethanesulfonamido)benzenesulfonamide (2 g) and triethylamine (0.7 g) in tetrahydrofuran (20 ml), propionyl chloride (0.45 g) was added, and the resultant mixture was allowed to stand at room temperature overnight. The reaction mixture was concentrated, admixed with 5% hydrochloric acid and extracted with chloroform. The extract was concentrated to give an oily substance, which was purified by silica gel chromatography. Recrystallization from a mixture of toluene and hexane gave 1.17 g of N-methyl-2,4-dimethyl-5-(N-propionyl-N-trifluoromethanesulfonylamino)benzenesulfonamide (Compound No. 16). M.P., 101°–103° C.

Examples of the trifluoromethanesulfonanilides (I) produced by the same procedure as above are known in Table 1.

TABLE 1

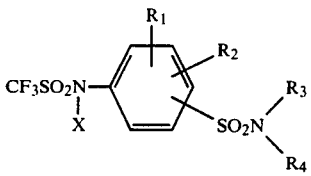

| Compound No. | X | $R_1$ | $R_2$ | $5\text{-}SO_2N\diagdown^{R_3}_{R_4}$ | Physical property |
|---|---|---|---|---|---|
| 1 | $CH_3CO-$ | 2-$CH_3$ | 4-$CH_3$ | 5-$SO_2N(CH_3)_2$ | M.P. 102–103° C. |
| 2 | $C_2H_5CO-$ | 2-$CH_3$ | 4-$CH_3$ | 5-$SO_2N(CH_3)_2$ | M.P. 122.5–123.5° C. |
| 3 | $CH_3(CH_2)_3CO-$ | 2-$CH_3$ | 4-$CH_3$ | 5-$SO_2N(CH_3)_2$ | M.P. 80–81° C. |
| 4 | $ClCH_2CO-$ | 2-$CH_3$ | 4-$CH_3$ | 5-$SO_2N(CH_3)_2$ | M.P. 127–132° C. |
| 5 | $CH_3CO-$ | 2-$CH_3$ | 4-$CH_3$ | 5-$SO_2N(CH_3)(CH_2C{\equiv}CH)$ | M.P. 72.5–74° C. |
| 6 | $CH_3CO-$ | 2-$CH_3$ | 4-$CH_3$ | 5-$SO_2N(CH_3)(CH_2CH_2CH_3)$ | $n_D^{19}$ 1.4995 |
| 7 | $CH_3CO-$ | 2-$CH_3$ | 4-$CH_3$ | 5-$SO_2N(CH_2C{\equiv}CH)_2$ | M.P. 108.5–109° C. |
| 8 | $CH_3CO-$ | 2-$CH_3$ | 4-$CH_3$ | 5-$SO_2N(CH_3)(COCH_3)$ | M.P. 83.5–87.5° C. |
| 9 | $C_2H_5CO-$ | 2-$CH_3$ | 4-$CH_3$ | 5-$SO_2N(CH_3)(COC_2H_5)$ | M.P. 95.5–96.5° C. |
| 10 | $CH_3CO-$ | 2-$CH_3$ | 4-$CH_3$ | 5-$SO_2N(CH_2C{\equiv}CH)(COCH_3)$ | $n_D^{20}$ 1.5209 |

TABLE 1-continued $$\text{(I)}$$

Structure: A benzene ring with $CF_3SO_2N(X)-$ at one position, $R_1$, $R_2$, and $SO_2NR_3R_4$ substituents.

| Compound No. | X | $R_1$ | $R_2$ | $SO_2N(R_3)(R_4)$ | Physical property |
|---|---|---|---|---|---|
| 11 | $CH_3CO-$ | 2-$CH_3$ | 4-$CH_3$ | 5-$SO_2N(CH_2CH=CH_2)(COCH_3)$ | M.P. 105–106° C. |
| 12 | $CH_3CO-$ | 2-$CH_3$ | 4-$CH_3$ | 5-$SO_2NHC_2H_5$ | M.P. 139.5–141° C. |
| 13 | $CH_3CO-$ | 2-$CH_3$ | 4-$CH_3$ | 5-$SO_2NHCH_3$ | M.P. 123.5–128.5° C. |
| 14 | $CH_3CO-$ | 2-$CH_3$ | 4-$CH_3$ | 5-$SO_2NHCH_2CH=CH_2$ | M.P. 107–110° C. |
| 15 | $CH_3CO-$ | 2-$CH_3$ | 4-$CH_3$ | 5-$SO_2NHCH_2C\equiv CH$ | M.P. 126–127.5° C. |
| 16 | $C_2H_5CO-$ | 2-$CH_3$ | 4-$CH_3$ | 5-$SO_2NHCH_3$ | M.P. 101–103° C. |
| 17 | $CH_3CO-$ | 2-$CH_3$ | 4-$CH_3$ | 5-$SO_2NHCOCH_3$ | Resinous material |
| 18 | $CH_3CO-$ | 2-Cl | 4-$CH_3$ | 5-$SO_2NHCH_3$ | M.P. 137–139° C. |
| 19 | $CH_3CO-$ | 2-$CH_3$ | 4-Cl | 5-$SO_2N(CH_3)(COCH_3)$ | M.P. 127.5–129° C. |
| 20 | $CH_3CO-$ | 2-$CH_3$ | 3-$CH_3$ | 5-$SO_2NHCH_3$ | $n_D^{27.5}$ 1.5063 |
| 21 | $CH_3CO-$ | 2-$CH_3$ | H | 4-$SO_2N(CH_3)_2$ | M.P. 148–148.5° C. |
| 22 | $C_2H_5CO-$ | 2-$CH_3$ | H | 4-$SO_2N(CH_3)_2$ | M.P. 130.5–131.5° C. |
| 23 | $(n)C_3H_7CO-$ | 2-$CH_3$ | H | 4-$SO_2N(CH_3)_2$ | M.P. 98–98.5° C. |
| 24 | $(iso)C_3H_7CO-$ | 2-$CH_3$ | H | 4-$SO_2N(CH_3)_2$ | M.P. 101–102° C. |
| 25 | $CH_3CH=CHCO-$ | 2-$CH_3$ | H | 4-$SO_2N(CH_3)_2$ | M.P. 110.5–114° C. |
| 26 | $CH_3CO-$ | 2-$CH_3$ | H | 4-$SO_2NHC_4H_9(t)$ | M.P. 94–97.5° C. |
| 27 | $C_2H_5CO-$ | 2-$CH_3$ | H | 4-$SO_2NHC_4H_9(t)$ | M.P. 114.5–115° C. |
| 28 | $(n)C_3H_7CO-$ | 2-$CH_3$ | H | 4-$SO_2NHC_4H_9(t)$ | M.P. 87.5–88.5° C. |

TABLE 1-continued $$\text{(I)}$$

Structure: benzene ring with CF$_3$SO$_2$N(X)— at one position, R$_1$, R$_2$, and —SO$_2$NR$_3$R$_4$ substituents.

| Compound No. | X | R$_1$ | R$_2$ | SO$_2$NR$_3$R$_4$ | Physical property |
|---|---|---|---|---|---|
| 29 | CH$_3$CO— | 2-CH$_3$ | H | 4-SO$_2$N(CH$_3$)(C(=O)CH$_3$) | M.P. 130–131.5° C. |
| 30 | CH$_3$CO— | 2-CH$_3$ | H | 4-SO$_2$NHCH$_3$ | M.P. 98.5–100° C. |

Some examples for the production of the starting compounds, i.e. trifluoromethanesulfonanilide (II), are shown below.

EXAMPLE 4

A mixture of a 40% aqueous solution of methylamine (0.7 g), 4-(trifluoromethanesulfonamido)benzenesulfonyl chloride (1.5 g) and water (20 ml) was allowed to stand overnight and made acidic with hydrochloric acid to precipitate crystals, which were then recrystallized from a mixture of water and ethanol to give 0.65 g of N-methyl-4-(trifluoromethanesulfonamido)benzenesulfonamide. M.P., 156°–157° C.

EXAMPLE 5

A solution of t-butylamine (0.6 g) and 3-chloro-4-(trifluoromethanesulfonamido)benzenesulfonyl chloride (1.5 g) in tetrahydrofuran (20 ml) was allowed to stand overnight. The resultant mixture was concentrated and shaken with chloroform and 5% aqueous hydrochloric acid. The chloroform extract was concentrated and recrystallized from toluene to give 1.03 g of N-t-butyl-3-chloro-4-(trifluoromethanesulfonamido)benzenesulfonamide. M.P., 123°–127.5° C.

EXAMPLE 6

A solution of diethylamine (1 g) and 3-methyl-4-(trifluoromethanesulfonamido)benzenesulfonyl chloride (1.5 g) in tetrahydrofuran (20 ml) was allowed to stand overnight. The resultant mixture was concentrated and shaken with chloroform and 5% aqueous hydrochloric acid. The chloroform extract was concentrated and recrystallized from a mixture of ethanol and water to give 0.97 g of N,N-diethyl-3-methyl-4-(trifluoromethanesulfonamido)benzenesulfonamide. M.P., 128°–128.5° C.

EXAMPLE 7

A mixture of 2,4-dimethyl-5-(trifluoromethanesulfonamido)benzenesulfonyl chloride (1.5 g), a 40% aqueous solution of methylamine (1 g) and water (20 ml) was stirred at room temperature and allowed to stand overnight at the same temperature. The resultant mixture was made acidic with 5% aqueous hydrochloric acid to precipitate an oily substance, which was then extracted with chloroform. The organic layer was washed with a 5% aqueous solution of hydrochloric acid and water in order and dried over anhydrous magnesium sulfate, followed by concentration. The residue was allowed to stand to give crystals, which were recrystallized from toluene to give 1.1 g of N-methyl-2,4-dimethyl-5-(trifluoromethanesulfonamido)benzenesulfonamide. M.P., 134.5°–135.5° C.

EXAMPLE 8

2,4-Dimethyl-5-(trifluoromethanesulfonamido)benzenesulfonyl chloride (1.5 g) was added to tetrahydrofuran (20 ml) containing propargylamine (0.5 g), and the resultant mixture was allowed to stand overnight at room temperature. Upon completion of the reaction, the mixture was concentrated. A 5% aqueous solution of hydrochloric acid was added to the residue, whereby an oily substance was deposited. The oily substance was extracted with chloroform and washed with a 5% aqueous solution of hydrochloric acid and water in order. The extract was concentrated and recrystallized from toluene to give 1.05 g of N-propargyl-2,4-dimethyl-5-(trifluoromethanesulfonamido)benzenesulfonamide. M.P., 130.5°–132° C.

EXAMPLE 9

2,4-Dimethyl-3-(trifluoromethanesulfonamido)benzenesulfonyl chloride (1.4 g) was added to tetrahydrofuran (20 ml) containing dimethylamine (0.6 g), and the resultant mixture was allowed to stand overnight at room temperature. The reaction mixture was concentrated, admixed with 5% hydrochloric acid and extracted with chloroform. The extract was washed with 5% hydrochloric acid and water in order, dried over anhydrous magnesium sulfate and concentrated to give an oily substance, which was purified by column chromatography with silica gel (150 ml) to give 1.0 g of N,N-dimethyl-2,4-dimethyl-3-(trifluoromethanesulfonamido)benzenesulfonamide. M.P., 70.5°–72° C.

EXAMPLE 10

To a solution of triethylamine (1.33 g) and N-ethyl-3-aminobenzenesulfonamide (2.5 g) in chloroform (50 ml), trifluoromethanesulfonic anhydride (3.6 g) was dropwise added while stirring. Upon completion of the addition, the resultant mixture was heated and refluxed for 3 hours. The reaction mixture was washed with 5% hydrochloric acid and concentrated to give a solid substance which was purified by silica gel column chromatography to give 1.88 g of N-ethyl-3-(trifluoromethanesulfonamido)benzenesulfonamide. M.P., 120.5°–124.5° C.

EXAMPLE 11

3-Methyl-4-(trifluoromethanesulfonamido)benzenesulfonyl chloride (1.5 g) was added to tetrahydrofuran (40 ml) containing t-butylamine (0.65 g), and the resultant mixture was allowed to stand at room temperature overnight. The reaction mixture was concentrated and extracted with chloroform. The extract was washed with 5% hydrochloric acid and water in order, dried over anhydrous magnesium sulfate and concentrated. The residue was recrystallized from benzene and then from toluene to give 0.57 g of N-t-butyl-3-methyl-4-(trifluoromethanesulfonamido)benzenesulfonamide. M.P., 139.5°–140.5° C.

Some specific examples of the trifluoromethanesulfonanilides (II) produced in the same manner as above are shown in Table 2.

TABLE 2

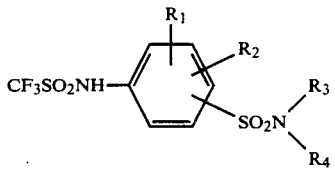

(II)

| $R_1$ | $R_2$ | $SO_2N\!\!<\!\!{}^{R_3}_{R_4}$ | Physical property |
|---|---|---|---|
| H | H | 4-SO$_2$N(CH$_3$)$_2$ | M.P. 172.5–173.5° C. |
| 2-CH$_3$ | H | 4-SO$_2$N(CH$_3$)$_2$ | M.P. 161–161.5° C. |
| 2-CH$_3$ | H | 4-SO$_2$N(CH$_3$)(C$_3$H$_7$(n)) | M.P. 112–113° C. |
| 2-CH$_3$ | H | 4-SO$_2$N(CH$_3$)(CH$_2$C≡CH) | M.P. 111–112° C. |
| 2-CH$_3$ | H | 4-SO$_2$N(C$_3$H$_7$(n))$_2$ | M.P. 116.5–117.5° C. |
| 2-CH$_3$ | H | 4-SO$_2$N(C$_2$H$_5$)(C$_3$H$_7$(n)) | M.P. 104.5–106.5° C. |
| 2-CH$_3$ | H | 4-SO$_2$N(CH$_3$)(OCH$_3$) | M.P. 114.5–115.5° C. |

TABLE 2-continued (II)

| $R_1$ | $R_2$ | $SO_2N\!\!<\!\!{}^{R_3}_{R_4}$ | Physical property |
|---|---|---|---|
| 2-CH$_3$ | H | 4-SO$_2$NHCH$_3$ | M.P. 132–132.5° C. |
| 2-CH$_3$ | H | 4-SO$_2$NHC$_2$H$_5$ | M.P. 91–93.5° C. |
| 2-CH$_3$ | H | 4-SO$_2$NHC$_3$H$_7$(iso) | M.P. 124.5–125° C. |
| 2-CH$_3$ | H | 4-SO$_2$NHCH$_2$CH=CH$_2$ | M.P. 101–103° C. |
| 2-CH$_3$ | H | 4-SO$_2$NH–C(CH$_3$)$_2$–C≡CH | M.P. 124.5–125.5° C. |
| 2-CH$_3$ | H | 4-SO$_2$NH–cyclohexyl | M.P. 119–120° C. |
| 2-Cl | H | 4-SO$_2$N(CH$_3$)$_2$ | M.P. 158–159° C. |
| 2-F | H | 4-SO$_2$N(CH$_3$)$_2$ | M.P. 163.5–164° C. |
| H | 3-CH$_3$ | 4-SO$_2$N(CH$_3$)$_2$ | M.P. 115.5–117.5° C. |
| 2-C$_2$H$_5$ | H | 4-SO$_2$N(CH$_3$)$_2$ | M.P. 122–123° C. |
| 2-CH$_3$ | 3-CH$_3$ | 4-SO$_2$N(CH$_3$)$_2$ | M.P. 141–143° C. |
| 2-CH$_3$ | 3-CH$_3$ | 4-SO$_2$N(CH$_3$)(OCH$_3$) | M.P. 122.5–123.5° C. |
| 2-CH$_3$ | 3-CH$_3$ | 4-SO$_2$NHC$_2$H$_5$ | M.P. 106.5–108.5° C. |
| 2-CH$_3$ | 5-CH$_3$ | 4-SO$_2$N(CH$_3$)$_2$ | M.P. 165–166.5° C. |
| 2-CH$_3$ | H | 4-SO$_2$N(morpholino) | M.P. 174.5–175.5° C. |
| 2-CH$_3$ | H | 5-SO$_2$N(CH$_3$)$_2$ | M.P. 110–113.5° C. |

TABLE 2-continued (II) Structure: CF₃SO₂NH—[benzene with R₁, R₂]—SO₂NR₃R₄

| R₁ | R₂ | SO₂NR₃R₄ | Physical property |
|---|---|---|---|
| 2-CH₃ | 4-CH₃ | 5-SO₂NHC₂H₅ | M.P. 126.5–127.5° C. |
| 2-CH₃ | 4-CH₃ | 5-SO₂NHC₃H₇(n) | M.P. 120.5–121° C. |
| 2-CH₃ | 4-CH₃ | 5-SO₂NHC₃H₇(iso) | M.P. 140–141.5° C. |
| 2-CH₃ | 4-CH₃ | 5-SO₂NH—(cyclopropyl) | M.P. 139.5–141° C. |
| 2-CH₃ | 4-CH₃ | 5-SO₂NHCH₂CH=CH₂ | M.P. 115–116° C. |
| 2-CH₃ | 4-CH₃ | 5-SO₂NHC₄H₉(t) | M.P. 169–171° C. |
| 2-CH₃ | 4-CH₃ | 5-SO₂NH—C(CH₃)₂—C≡CH | M.P. 179–181° C. |
| 2-CH₃ | 4-CH₃ | 5-SO₂NHCH₂CH₂OCH₃ | M.P. 95–96° C. |
| 2-CH₃ | 4-CH₃ | 5-SO₂NHCH₂CH₂OC₂H₅ | M.P. 101–102° C. |
| 2-CH₃ | 4-CH₃ | 5-SO₂NHCH₂CH(OCH₃)₂ | $n_D^{24.5}$ 1.4881 |
| 2-CH₃ | 4-CH₃ | 5-SO₂NH(CH₂)₃OCH₃ | $n_D^{24.5}$ 1.4963 |
| 2-CH₃ | 4-CH₃ | 5-SO₂NHCH₂—C(CH₃)=CH₂ | M.P. 103.5–104.5° C. |
| 2-CH₃ | 4-CH₃ | 5-SO₂N(CH₃)₂ | M.P. 82.5–83.5° C. |
| 2-CH₃ | 4-CH₃ | 5-SO₂N(C₂H₅)₂ | M.P. 78.5–80° C. |
| 2-CH₃ | 4-CH₃ | 5-SO₂N(CH₃)(CH₂C≡CH) | M.P. 87.5–89° C. |
| 2-CH₃ | 4-CH₃ | 5-SO₂N(CH₃)(C₃H₇(n)) | M.P. 105–106° C. |
| 2-CH₃ | 4-CH₃ | 5-SO₂N(CH₂C≡CH)₂ | M.P. 89–90° C. |
| 2-CH₃ | 4-CH₃ | 5-SO₂N(CH₃)(OCH₃) | M.P. 89.5–90° C. |
| 2-CH₃ | 4-CH₃ | 5-SO₂N(CH₃)(CH₂—C₆H₅) | $n_D^{22}$ 1.5239 |
| 2-CH₃ | 4-CH₃ | 5-SO₂NH—CH(CH₃)—C₆H₅ | M.P. 164.5–165.5° C. |
| 2-Cl | 4-CH₃ | 5-SO₂NHCH₃ | M.P. 161–161.5° C. |
| 2-Cl | 4-CH₃ | 5-SO₂NHC₂H₅ | M.P. 107–109° C. |
| 2-Cl | 4-CH₃ | 5-SO₂NHCH₂CH=CH₂ | M.P. 105.5–106.5° C. |
| 2-Cl | 4-CH₃ | 5-SO₂NHCH₂C≡CH | M.P. 131.5–134° C. |
| 2-Cl | 4-CH₃ | 5-SO₂N(CH₃)₂ | M.P. 119.5–120° C. |
| 2-CH₃ | 4-Cl | 5-SO₂NHCH₃ | M.P. 178.5–179° C. |
| 2-CH₃ | 4-Cl | 5-SO₂NHC₂H₅ | M.P. 141–142° C. |
| 2-CH₃ | 4-Cl | 5-SO₂N(CH₃)₂ | M.P. 128–129° C. |
| 2-CH₃ | 4-CH₃ | 5-SO₂N(morpholino) | M.P. 138.5–139.5° C. |
| 2-CH₃ | 6-CH₃ | 3-SO₂NHCH₃ | M.P. 117–118° C. |
| 2-CH₃ | 6-CH₃ | 3-SO₂NHC₂H₅ | M.P. 134.5—136° C. |
| 2-CH₃ | 6-CH₃ | 3-SO₂NHC₄H₉(t) | M.P. 156–156.5° C. |
| 2-CH₃ | 3-CH₃ | 5-SO₂NHCH₃ | M.P. 83–87° C. |

Some examples for the production of the intermediary compound, i.e. benzenesulfonyl chloride (V), are shown below:

EXAMPLE 12

Production of the benzenesulfonyl chloride (V: R₁=2—CH₃; R₂=H; 4—SO₂Cl):

To a solution of 2-methyltrifluoromethanesulfonanilide (15 g) in chloroform (200 ml), chlorosulfonic acid (18.3 g) was dropwise added while maintaining the temperature between 0° and 5° C. After completion of the addition, the temperature was raised to room temperature, and the resultant mixture was stirred for about 1 hour and then heated under reflux for 3 hours. The reaction mixture was washed with water, and the chloroform layer was dried over anhydrous magnesium sulfate and concentrated. The residue was recrystallized from toluene to give 8.1 g of 3-methyl-4-(trifluoromethanesulfonamido)benzenesulfonyl chloride. M.P., 112°–114° C.

EXAMPLE 13

Production of the benzenesulfonyl chloride (V: $R_1=2$—$CH_3$; $R_2=4$—$CH_3$; 5—$SO_2Cl$):

To a solution of 2,4-dimethyltrifluoromethanesulfonanilide (30 g) in chloroform (40 ml), chlorosulfonic acid (44.8 g) was dropwise added while maintaining the temperature between 0° and 5° C. After completion of the addition, the temperature was raised to room temperature, and the resultant mixture was stirred for about 1 hour and then heated under reflux for 3 hours. The reaction mixture was washed with water, and the chloroform layer was dried over anhydrous magnesium sulfate and concentrated. The residue was recrystallized from toluene to give 34.2 g of 2,4-dimethyl-5-(trifluoromethanesulfonamido)benzenesulfonyl chloride. M.P., 122°–124.5° C.

Some specific examples of the benzenesulfonyl chlorides (V) produced in the same manner as above are shown in Table 3.

TABLE 3

$$CF_3SO_2NH-\underset{\underset{SO_2Cl}{}}{\overset{\overset{R_1}{}}{\bigcirc}}-R_2 \quad (V)$$

| $R_1$ | $R_2$ | $SO_2Cl$ | Physical property |
|---|---|---|---|
| H | H | 4-$SO_2Cl$ | M.P. 91.5–93.5° C. |
| 2-$CH_3$ | H | 4-$SO_2Cl$ | M.P. 112–114° C. |
| 2-Cl | H | 4-$SO_2Cl$ | M.P. 93.5–95° C. |
| 2-F | H | 4-$SO_2Cl$ | M.P. 90.5–93° C. |
| 2-$C_2H_5$ | H | 4-$SO_2Cl$ | M.P. 55–57° C. |
| 3-$CH_3$ | H | 4-$SO_2Cl$ | M.P. 73–75.5° C. |
| 2-$CH_3$ | 5-$CH_3$ | 4-$SO_2Cl$ | M.P. 151.5–154° C. |
| 2-$CH_3$ | 3-$CH_3$ | 4-$SO_2Cl$ | M.P. 97.5–99° C. |
| 2-$CH_3$ | 6-$CH_3$ | 3-$SO_2Cl$ | M.P. 122.5–124° C. |
| 2-$CH_3$ | 4-$CH_3$ | 5-$SO_2Cl$ | M.P. 122–124.5° C. |
| 2-$CH_3$ | 4-Cl | 5-$SO_2Cl$ | M.P. 110.5–112.5° C. |
| 2-Cl | 4-$CH_3$ | 5-$SO_2Cl$ | M.P. 111.5–112.5° C. |

In the practical usage of the trifluoromethanesulfonanilides (I), they may be applied as such or in any composition form such as emulsifiable concentrates, wettable powders, suspensions, granules or dusts.

For formulation of those compositions, a solid or liquid carrier or diluent may be used. As for the solid carrier or diluent, there may be mentioned mineral powders (e.g. kaolin, bentonite, talc, diatomaceous earth, sericite, synthetic hydrated silica), etc. As for the liquid carrier or diluent, there may be exemplified aromatic hydrocarbons (e.g. xylene, methylnaphthalene), ketones (e.g. cyclohexanone, isophorone), chlorobenzene, dimethylformamide, cellosolve, ethylene glycol, water, etc.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene styrylaryl ethers, polyoxyethylene fatty acid esters, polyoxyethylene sorbitan fatty acid esters, oxyethyleneoxypropylene polymers, alkyl sulfates, alkyl sulfonates, dialkyl sulfosuccinates, alkylaryl sulfonates and the like. If necessary, lignin sulfonates, polyvinyl alcohols, cellulose derivatives (e.g. methylcellulose), isopropyl acid phosphate, alginates or the like may be used as auxiliary agents.

The trifluoromethanesulfonanilides (I) of the invention may be used together with other herbicides to improve their activity as herbicides, and in some cases, a synergistic effect can be expected. Further, they may be also applied in combination with insecticides, nematocides, fungicides, plant growth regulators, fertilizers, etc. depending upon need.

In the herbicidal composition of the invention, the content of the trifluoromethanesulfonanilides (I) may be from 0.1 to 90% by weight, preferably from 1 to 80% by weight.

Practical embodiments of the herbicidal composition according to the invention are illustratively shown in the following examples wherein parts and % are by weight. The compound number of the active ingredient corresponds to the one in Table 1.

FORMULATION EXAMPLE 1

Eighty parts of Compound No. 3, 5 parts of polyoxyethylene alkylaryl ether and 15 parts of synthetic hydrated silica are well mixed while being powdered to obtain a wettable powder.

FORMULATION EXAMPLE 2

Ten parts of Compound No. 16, 7 parts of polyoxyethylene alkylaryl ether, 3 parts of alkylarylsulfonate and 80 parts of cyclohexanone are well mixed while being powdered to obtain an emulsifiable concentrate.

FORMULATION EXAMPLE 3

One part of Compound No. 7, 1 part of synthetic hydrated silica, 5 parts of lignin sulfonate and 93 parts of kaolin are well mixed while being powdered. The mixture is then kneaded with water, granulated and dried to obtain granules.

FORMULATION EXAMPLE 4

Three parts of Compound No. 1, 0.5 part of isopropyl acid phosphate, 66.5 parts of kaolin and 30 parts of talc are well mixed while being powdered to obtain a dust.

FORMULATION EXAMPLE 5

Twenty parts of Compound No. 8 is mixed with 60 parts of an aqueous solution containing 3% polyoxyethylene sorbitan monooleate and grained until the particle size of the active ingredient becomes less than 3 microns. Twenty parts of an aqueous solution containing 3% of sodium alginate as a dispersing agent is incorporated therein to obtain a suspension.

The dosage rate of the trifluoromethanesulfonanilides (I) may vary on the kind of weeds, the growing status of weeds, the field of application, the sort of crop plants, the mode of application, the weather condition, the kind of composition form, etc. Generally, however, the dosage rate may be from 1 to 100 grams, preferably from 2 to 50 grams, of the active ingredient per are.

The application of the trifluoromethanesulfonanilides (I) as herbicides will be illustratively shown in the following Examples wherein the phytotoxicity to crop plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the phytotoxicity and the herbicidal activity were evaluated by the standard given in the table below. The rating values of phytotoxicity, 0 and 1, and those of herbicidal activity, 5 and 4, are generally regarded as satisfactory to protect crop plants and to control weeds, respectively. The rating values in the paddy field test alone were calculated from the dry weight of the test plants.

| Rating value | Fresh weight (percentage to untreated plot) (%) | |
|---|---|---|
| | Herbicidal activity | Phytotoxicity |
| 0 | 91– | 91– |
| 1 | 71–90 | 71–90 |
| 2 | 41–70 | 51–70 |
| 3 | 11–40 | 31–50 |
| 4 | 1–10 | 11–30 |
| 5 | 0 | 0–10 |

The following compounds were used in the Examples for comparison:

| Compound No. | Chemical structure | Remarks |
|---|---|---|
| A | ⌬—SO$_2$—⌬(CH$_3$)—NHSO$_2$CF$_3$ | British patent 1,306,564 (known as "perfluidone") |
| B | CF$_3$SO$_2$NH—⌬—SO$_2$NH$_2$ | U.S. Pat. No. 3,639,474 |

TEST EXAMPLE 1

Plastic pots (500 ml volume) were filled with upland field soil and seeds of Johnsongrass, green foxtail, annual bluegrass, tall morningglory, velvetleaf, common chickweed and pineappleweed were sowed therein. A designed amount of the test compound formulated into an emulsifiable concentrate according to Formulation Example 2 and dispersed in water was sprayed to the soil surface by means of a small hand sprayer at a spray volume of 10 liters per are. Thereafter, the soil surface was mixed well to the depth of 3 cm. The seeds of soybean, cotton and sugarbeet were sowed and the tubers of purple nutsedge and the rhizome of Johnsongrass were transplanted to the pots at the depth of 2 cm from the soil surface. Cultivation was made in a greenhouse for 3 weeks, and the herbicidal activity and the phytotoxicity were examined. The results are shown in Table 4.

TABLE 4

| Compound No. | Dosage (weight of active ingredient, g/are) | Herbicidal activity | | | | | | | | | Phytotoxicity | | |
|---|---|---|---|---|---|---|---|---|---|---|---|---|---|
| | | Johnson-grass | Green foxtail | Annual bluegrass | Tall morning-glory | Velvet-leaf | Common chick-weed | Pine-apple-weed | Purple nut-sedge | Johnson-grass rhizome | Soy-bean | Cot-ton | Sugar-beet |
| 1 | 40 | 5 | 5 | 5 | 5 | 5 | 5 | 5 | 5 | 5 | — | — | — |
| | 10 | 5 | 4 | 5 | 5 | 5 | 5 | 5 | 5 | 4 | 2 | 1 | — |
| 2 | 40 | 5 | 5 | 5 | 5 | 5 | 5 | 5 | 5 | — | — | — | — |
| | 10 | 5 | 5 | 5 | 5 | 5 | 5 | 4 | 5 | — | 1 | 1 | — |
| 3 | 40 | 5 | 5 | 5 | 5 | 5 | 5 | 5 | 5 | 5 | — | — | — |
| | 10 | 4 | 5 | 5 | 5 | 5 | 5 | 5 | 5 | 4 | — | 1 | — |
| 4 | 40 | 5 | 5 | 5 | 5 | 5 | 5 | 5 | 5 | 5 | 2 | — | — |
| | 10 | 4 | 4 | 5 | 5 | 5 | 5 | 5 | 5 | — | 0 | — | — |
| 5 | 40 | 5 | 5 | 5 | 5 | 5 | 5 | 5 | 5 | 5 | 2 | — | — |
| | 10 | 4 | 4 | 5 | 5 | 4 | 5 | 5 | 5 | — | 0 | — | — |
| 6 | 40 | 5 | 5 | 5 | 5 | 5 | 5 | 5 | 5 | 4 | — | — | — |
| | 10 | 5 | 5 | 5 | 2 | 5 | 5 | 5 | 4 | — | 1 | 1 | — |
| 7 | 40 | 5 | 5 | 5 | 3 | 5 | 5 | 5 | 5 | — | — | — | — |
| | 10 | 5 | 5 | 5 | 2 | 4 | 4 | 5 | 4 | — | 1 | 1 | — |
| 8 | 40 | 5 | 5 | 5 | 5 | 5 | 5 | 5 | 5 | 5 | — | — | — |
| | 10 | 4 | 4 | 5 | 5 | 5 | 5 | 5 | 4 | — | — | 1 | — |
| 9 | 40 | 5 | 5 | 5 | 5 | 5 | 5 | 5 | 5 | 5 | — | — | — |
| | 10 | 4 | 5 | 5 | 5 | 5 | 5 | 5 | 5 | — | — | 1 | — |
| 10 | 40 | 5 | 5 | 5 | 5 | 5 | 5 | 5 | 5 | 5 | — | — | — |
| | 10 | 4 | 4 | 5 | 5 | 5 | 5 | 5 | 5 | — | — | 1 | — |
| 11 | 40 | 5 | 5 | 5 | 5 | 5 | 5 | 5 | 5 | 4 | — | — | — |
| | 10 | 4 | 4 | 4 | 4 | 4 | 5 | 5 | 2 | — | 1 | 1 | — |
| 12 | 40 | 5 | 5 | 5 | 5 | 5 | 5 | 5 | 5 | — | — | 2 | — |
| | 10 | — | 4 | 5 | 5 | 5 | 5 | 5 | 5 | — | — | 0 | 1 |
| 13 | 40 | 5 | 5 | 5 | 5 | 5 | 5 | 5 | 5 | 5 | — | — | — |
| | 10 | 4 | 5 | 5 | 5 | 5 | 5 | 5 | 5 | — | 1 | — | — |
| 14 | 40 | 5 | 5 | 5 | 5 | 5 | 5 | 5 | 5 | 5 | — | — | — |
| | 10 | 4 | — | 5 | 5 | 4 | 5 | 5 | — | — | — | 0 | — |
| 15 | 40 | 5 | 5 | 5 | 5 | 5 | 5 | 5 | 5 | 5 | — | — | — |
| | 10 | 4 | 4 | 5 | 4 | 4 | 5 | 5 | 4 | — | — | 1 | — |
| 16 | 40 | 5 | 5 | 5 | 5 | 5 | 5 | 5 | 5 | 5 | — | — | — |
| | 10 | 4 | 5 | 5 | 5 | 5 | 5 | 5 | 5 | — | 2 | — | — |
| 17 | 40 | 5 | 5 | 5 | 5 | 5 | 5 | 5 | 5 | 5 | — | — | — |
| | 10 | 5 | 4 | 5 | 3 | 4 | 4 | 5 | — | — | 1 | — | — |
| 18 | 40 | 5 | 5 | 5 | 5 | 5 | 5 | 5 | 5 | 5 | — | — | — |
| | 10 | 5 | 5 | 5 | 5 | 5 | 5 | 5 | 5 | — | — | 2 | — |
| 19 | 40 | 5 | 5 | 5 | 5 | 5 | 5 | 5 | 5 | — | — | — | — |
| | 10 | 4 | 5 | 5 | 5 | 4 | 5 | 5 | 5 | — | — | 1 | — |
| 20 | 40 | 5 | 5 | 5 | 5 | 5 | 5 | 5 | 5 | 5 | — | — | — |
| | 10 | 5 | 5 | 5 | 5 | 5 | 5 | 5 | 5 | — | — | 2 | — |
| 21 | 40 | 5 | 5 | 5 | 5 | 5 | 5 | 5 | 5 | 4 | 2 | 1 | — |
| | 10 | 5 | 5 | 5 | 4 | 5 | 5 | 5 | 5 | — | 1 | 0 | — |
| 22 | 40 | 5 | 5 | 5 | 5 | 5 | 5 | 5 | 5 | 5 | — | 2 | 2 |

TABLE 4-continued

| Compound No. | Dosage (weight of active ingredient, g/are) | Herbicidal activity ||||||||| Phytotoxicity |||
|---|---|---|---|---|---|---|---|---|---|---|---|---|---|
| | | Johnson-grass | Green fox-tail | Annual blue-grass | Tall morning-glory | Velvet-leaf | Common chick-weed | Pine-apple-weed | Purple nut-sedge | Johnson-grass rhizome | Soy-bean | Cot-ton | Sugar-beet |
| 23 | 10 | 5 | 5 | 5 | 5 | 5 | 5 | 5 | 5 | 4 | 1 | 0 | 1 |
|  | 40 | 5 | 5 | 5 | 5 | 5 | 5 | 5 | 5 | 5 | — | — | — |
| 24 | 10 | 5 | 5 | 5 | 4 | 5 | 5 | 5 | 5 | 4 | 1 | 0 | 1 |
|  | 40 | 5 | 5 | 5 | 5 | 5 | 5 | 5 | 5 | 5 | — | — | — |
| 25 | 10 | 5 | 5 | 5 | 4 | 5 | 5 | 5 | 5 | 4 | 1 | 1 | 1 |
|  | 40 | 5 | 5 | 5 | 5 | 5 | 5 | 5 | 5 | 5 | — | 2 | — |
| 26 | 10 | — | 5 | 5 | 4 | 5 | 5 | 5 | 5 | 4 | 1 | 1 | 1 |
|  | 40 | 5 | 5 | 5 | 5 | 5 | 5 | 5 | 5 | 5 | 2 | 1 | — |
| 27 | 10 | 5 | 5 | 5 | 5 | 5 | 5 | 5 | 5 | 5 | 0 | 0 | — |
|  | 40 | 5 | 5 | 5 | 5 | 5 | 5 | 5 | 5 | 5 | — | — | — |
| 28 | 10 | 5 | 4 | 5 | 5 | 4 | — | 5 | 5 | 4 | 0 | 1 | 1 |
|  | 40 | 5 | 5 | 5 | 5 | 5 | 5 | 5 | 5 | 5 | — | — | — |
| 29 | 10 | 5 | 5 | 5 | 5 | 5 | — | 5 | 4 | 4 | 0 | 0 | 1 |
|  | 40 | 5 | 5 | 5 | 5 | 5 | 5 | 5 | 5 | 5 | — | 1 | — |
| 30 | 10 | 5 | 5 | 5 | 5 | — | 5 | 5 | 5 | 4 | 1 | 0 | 1 |
|  | 40 | 5 | 5 | 5 | 5 | 5 | 5 | 5 | 5 | 5 | — | — | 2 |
| A | 10 | 5 | 5 | 5 | 4 | 4 | 5 | 5 | 5 | 4 | — | 0 | 0 |
|  | 40 | 4 | 5 | 5 | 5 | 5 | 5 | 5 | 5 | 0 | 3 | 2 | 3 |
|  | 10 | 2 | 2 | 4 | 4 | 3 | 1 | 4 | 3 | 0 | 0 | 0 | 1 |
|  | 2.5 | 1 | 2 | 2 | 0 | 1 | 0 | 0 | 0 | 0 | 0 | 0 | 0 |
| B | 40 | 1 | 2 | 4 | 2 | 0 | 2 | 0 | 0 | 0 | 1 | 1 | 2 |
|  | 10 | 0 | 0 | 1 | 0 | 0 | 0 | 0 | 0 | 0 | 0 | 0 | 1 |

TEST EXAMPLE 2

In plastic pots (500 ml volume) filled with upland field soil, the tubers of purple nutsedge were transplanted and cultivated in a greenhouse for 4 weeks. Separately, the seeds of barnyardgrass, wild oat, wild mustard and velvetleaf were sowed in the similar pots and grown for 10 weeks in the greenhouse. A designed amount of the test compound formulated into an emulsifiable concentrate according to Formulation Example 2 and dispersed in water with a spreading agent was sprayed to the foliage of the test plants by means of a small hand sprayer at a spray volume of 10 liters per are. The test plants were further grown for 3 weeks in the greenhouse, and the herbicidal activity was examined. The results are shown in Table 5.

Among the test plants, purple nutsedge was further grown for 2 weeks in the greenhouse, and the number of revived sprouts in the treated plot was compared with that in the untreated plot. Evaluation was made on the following criteria: A, no revival; B, 1–10% revival; C, 11–50% revival; D, more than 51% revival. The results are also shown in Table 5.

TABLE 5

| Compound No. | Dosage (weight of active ingredient, g/are) | Herbicidal activity ||||  Prevention of revival Purple nutsedge |
|---|---|---|---|---|---|---|
| | | Barn-yard-grass | Wild oat | Wild mustard | Velvet-leaf | |
| 6 | 40 | 5 | 3 | 5 | 5 | B |
| 7 | 40 | 5 | 5 | 5 | 5 | B |
| 8 | 40 | 4 | 2 | 5 | 5 | B |
| 13 | 40 | 5 | 3 | 5 | 5 | A |
| 17 | 40 | 3 | 3 | 5 | 5 | A |
| 19 | 40 | 5 | 5 | 5 | 5 | A |
| 23 | 40 | 4 | 5 | 5 | 5 | A |
| 25 | 40 | 3 | 4 | 5 | 5 | A |
| 29 | 40 | 4 | 5 | 4 | 5 | A |
| A | 40 | 4 | 1 | 3 | 4 | C |
| B | 40 | 0 | 1 | 0 | 0 | C |

What is claimed is:

1. A compound of the formula:

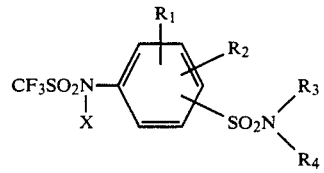

wherein $R_1$ and $R_2$ are, the same or different, each independently a hydrogen atom, a halogen atom or a $C_1$–$C_4$ alkyl group, $R_3$ and $R_4$ are, the same or different, each independently a hydrogen atom, a $C_1$–$C_4$ alkyl group, a $C_3$–$C_6$ cycloalkyl group, a $C_3$–$C_4$ alkenyl group, a $C_3$–$C_5$ alkynyl group, a $C_1$–$C_4$ alkoxy group, a $C_7$–$C_8$ hydrocarbyl aralkyl group, a $C_1$–$C_4$ alkoxy($C_1$–$C_4$)alkyl group or a $C_2$–$C_5$ acyl group and X is a $C_2$–$C_5$ and acyl group, provided that $R_3$ and $R_4$ are not simultaneously a hydrogen atom or a $C_2$–$C_5$ acyl group.

2. The compound according to claim 1, wherein $R_1$, $R_2$, $R_3$ and $R_4$ are each independently a hydrogen atom, a methyl group, an ethyl group or a t-butyl group and X is a $C_2$–$C_4$ alkanoyl group, provided that $R_3$ and $R_4$ are not simultaneously a hydrogen atom.

3. The compound according to claim 1, wherein $R_1$ is a methyl group at the 2-position, $R_2$ is a methyl group at the 4-position, $R_3$ is a propargyl group, $R_4$ is a methyl group, X is an acetyl group and the group of the formula:

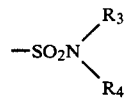

is present at the 5-position.

4. The compound according to claim 1, wherein $R_1$ is a methyl group at the 2-position, $R_2$ is a methyl group at the 4-position, $R_3$ is a propionyl group, $R_4$ is a methyl group, X is a propionyl group and the group of the formula:

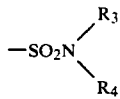

is present at the 5-position.

5. The compound according to claim 1, wherein $R_1$ is a methyl group at the 2-position, $R_2$ is a methyl group at the 4-position, $R_3$ is a methyl group, $R_4$ is a hydrogen atom, X is a propionyl group and the group of the formula:

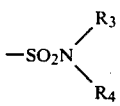

is present at the 5-position.

6. The compound according to claim 1, which is 4-(N-t-butylsulfamoyl)-2-methyl-N-butyryltrifluoromethanesulfonanilide.

7. A herbicidal composition which comprises as an active ingredient a herbicidally effective amount of a compound of the formula:

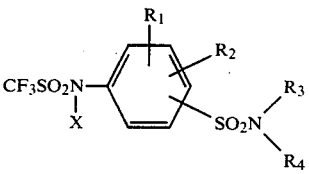

wherein $R_1$ and $R_2$ are, the same or different, each independently a hydrogen atom, a halogen atom or a $C_1$–$C_4$ alkyl group, $R_3$ and $R_4$ are, the same or different, each independently a hydrogen atom, a $C_1$–$C_4$ alkyl group, a $C_3$–$C_6$ cycloalkyl group, a $C_3$–$C_4$ alkenyl group, a $C_3$–$C_5$ alkynyl group, a $C_1$–$C_4$ alkoxy group, a $C_7$–$C_8$ hydrocarbyl aralkyl group, a $C_1$–$C_4$ alkoxy($C_1$–$C_4$)alkyl group or a $C_2$–$C_5$ acyl group and X is a $C_2$–$C_5$ acyl group, provided that $R_3$ and $R_4$ are not simultaneously a hydrogen atom or a $C_2$–$C_5$ acyl group, and an inert carrier.

8. A method for controlling weeds which comprises applying a herbicidally effective amount of a compound of the formula:

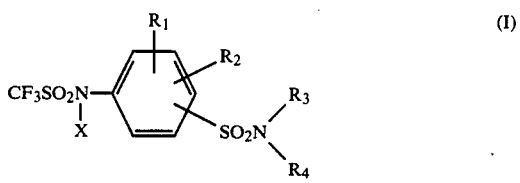

wherein $R_1$ and $R_2$ are, the same or different, each independently a hydrogen atom, a halogen atom or a $C_1$–$C_4$ alkyl group, $R_3$ and $R_4$ are, the same or different, each independently a hydrogen atom, a $C_1$–$C_4$ alkyl group, a $C_3$–$C_6$ cycloalkyl group, a $C_3$–$C_4$ alkenyl group, a $C_3$–$C_5$ alkynyl group, a $C_1$–$C_4$ alkoxy group, a $C_7$–$C_8$ hydrocarbyl aralkyl group, a $C_1$–$C_4$ alkoxy($C_1$–$C_4$)alkyl group or a $C_2$–$C_5$ acyl group and X is a $C_2$–$C_5$ acyl group, provided that $R_3$ and $R_4$ are not simultaneously a hydrogen atom or a $C_2$–$C_5$ acyl group, to the area where the weeds grow or will grow.

9. The method according to claim 8, wherein the area is a field of soybeans, cotton or sugarbeets.

* * * * *